United States Patent [19]

Scattergood et al.

[11] 4,136,684
[45] Jan. 30, 1979

[54] LINEAR ELECTROMYOGRAPHIC BIOFEEDBACK SYSTEM

[76] Inventors: Mark G. Scattergood; David C. Howson, both of R.D. 2, Trumansburg, N.Y. 14886

[21] Appl. No.: 766,500

[22] Filed: Feb. 7, 1977

[51] Int. Cl.² ............................................. A61B 5/05
[52] U.S. Cl. ................................. 128/2.1 M; 35/22 R
[58] Field of Search ............ 128/2.1 M, 2.1 R, 2.1 C, 128/2.1 B, 2.1 Z, 2.06 B; 35/22 R

[56] References Cited

U.S. PATENT DOCUMENTS

| | | | |
|---|---|---|---|
| 3,533,003 | 10/1970 | Plaszczynski et al. | 128/2.06 B X |
| 3,628,538 | 12/1971 | Vincent et al. | 128/2.1 M |
| 3,641,993 | 2/1972 | Gaarder et al. | 128/2.1 M |
| 3,753,433 | 8/1973 | Bakerich et al. | 128/2.1 B |
| 3,896,790 | 7/1975 | Dikmen | 128/2.1 B |
| 3,905,355 | 9/1975 | Brudny | 128/2.1 M |
| 3,978,847 | 9/1976 | Fehmi et al. | 128/2.1 B |
| 3,983,865 | 10/1976 | Shepard | 128/2.1 M |

FOREIGN PATENT DOCUMENTS 234604  6/1969  U.S.S.R. ............................... 128/2.1 M

OTHER PUBLICATIONS

Garland et al., "A Portable EMG Monitor," Med. Inst., vol. 8, No. 2, Mar.-Apr. 1974, p. 127.
Garland et al., "A State Variable Averaging Filter . . . Processing," Med. & Biol. Eng., vol. 10, pp. 559-560, 1972.
Post, "Electromyography," Radio-Electronics, Nov. 1960, pp. 34-37.
Waite, "Alpha Brain Wave Feedback Monitor," Popular Electronics, Jan. 1973, pp. 40-45.

*Primary Examiner*—Lee S. Cohen
*Attorney, Agent, or Firm*—George E. Clark

[57] ABSTRACT

A linear electromyographic biofeedback system operates over a dynamic range of at least one thousand to one. That is, the system remains linear from input levels of approximately one microvolt to input levels in excess of one millivolt. The linear electromyographic biofeedback system includes a sensitive transducer which is followed by a protection circuit and connected to a differential amplifier for eliminating common mode noise. The output of the differential amplifier is filtered and amplified to further eliminate unwanted signals. This filtered signal is rectified and averaged in a third order averaging filter to obtain a close approximation of a time averaging without the necessity of discrete timing periods. The output signal from the averaging filter is then used to control a current controlled oscillator which provides a series of audible pulses at a rate which varies linearly with the value of the input voltage detected by the transducer, the repetition rate range being from approximately one hertz to greater than five thousand hertz.

3 Claims, 4 Drawing Figures

U.S. Patent   Jan. 30, 1979   Sheet 1 of 3   4,136,684
FIG. 1
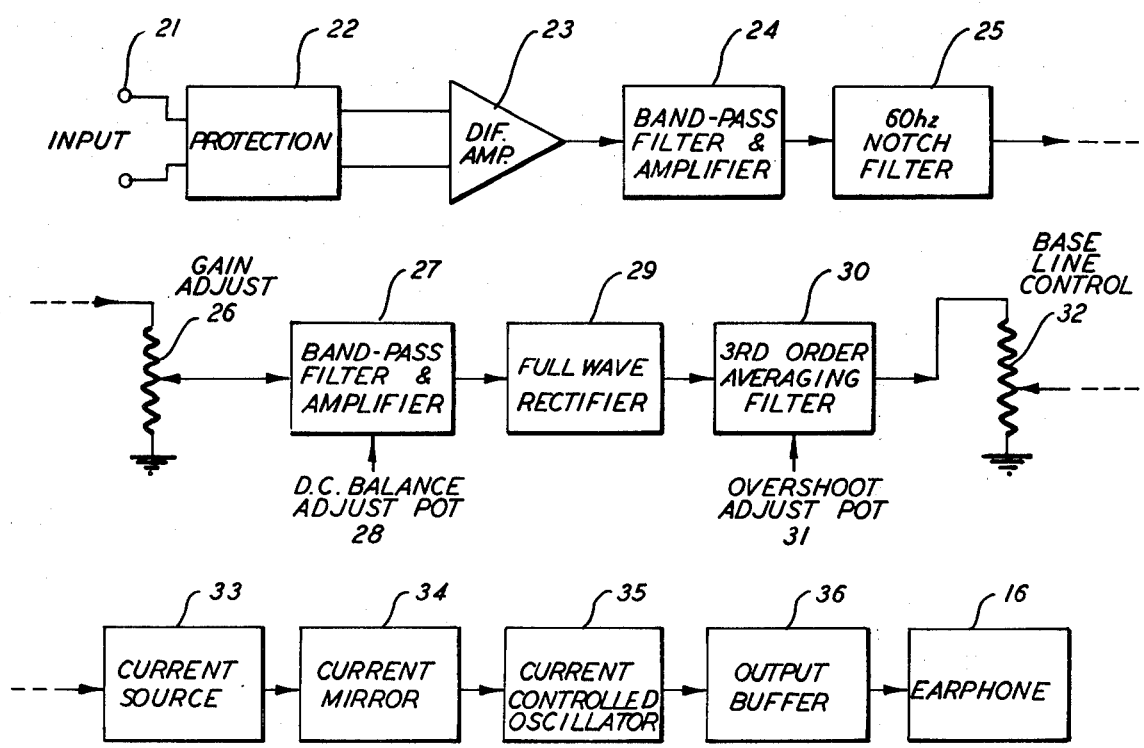
FIG. 2

LINEAR ELECTROMYOGRAPHIC BIOFEEDBACK SYSTEM

BACKGROUND OF THE INVENTION

1. Field of the Invention

The present invention relates to bioelectronic systems and more particularly, to electromyographic biofeedback systems.

2. Description of the Prior Art:

There are in the prior art, many systems which measure human muscle activity and provide an output signal which corresponds to the muscle activity. However, most of these prior art systems are limited in the range of operation and are basically digital in nature in that they do not provide any response below a preset threshold level. Therefore, the patient or the therapist gets no information relative to small muscle movements. In some cases, it is the small muscle movements which are most important since these are the movements which indicate the earliest signs of progress in rehabilitation.

Examples of the prior are threshold systems are U.S. Pat. No. 3,656,474 to Gentry, et al, and U.S. Pat. No. 3,657,646 to Zmyslowski, et al.

Another prior art electromyograph is shown by Gaarder, et al, in U.S. Pat. No. 3,641,993. Gaarder, et al, teaches an electromyograph in which the amplification system is non-linear and in fact is responsive to the logarithm of the peak value of the input signals representing human muscle activity. Gaarder, et al, includes a means to integrate the voltage representing muscle activity over a preset time interval. Because of the requirement for integration of the input voltage, the teaching of Gaarder, et al, is not appropriate for a real time biofeedback system. The patient must have an instantaneous response to any muscle activity. A delay which is required by an integration system will not give the patient the proper kind of feedback information for him to determine what was the cause of the signal which he received at any instant of time. Further, the logarithmic amplification of the input signal by the Gaarder, et al, system prevents a wide dynamic range of operation. The system distorts the rate of change of muscle activity in the higher voltage range. For example, the output frequency rate in the Gaarder, et al, system changes very little in the top portion of the range of muscle activity.

A biofeedback system, to operate effectively must provide an instantaneous signal to the human which can be translated by the brain into an indication of small muscle movement. For this reason, it is very important that an electromyographic biofeedback system be sensitive over a wide range of muscle activity. The response to a single muscle unit, the smallest measurable muscle unit, should be such as to provide the patient with an appropriate indication of muscle activity. Biofeedback of small muscle activity such as an indication of activity by a single muscle unit provides a very positive psychological effect on the patient in that the patient can hear or see a positive indication of progress in rehabilitation.

Also, it is very important to maintain a uniform sensitivity of the electromyographic biofeedback system over a wide range of muscle activity to provide the patient and the therapist with an accurate indication of progress in the rehabilitation.

Additionally, since most human systems, such as human hearing are logarithmic in nature, it is important that the external biofeedback system be linear to prevent distortion of the magnitude of the muscle activity signal to the human ear.

All of the prior art systems discussed have one or more deficiencies which are overcome by a linear electromyographic biofeedback system.

SUMMARY OF THE INVENTION

Accordingly, it is an object of the present invention to provide an output signal from an electromyograph for biofeedback purposes which accurately represents instantaneous muscle activity.

Another object of the present invention is to provide the output set out above in a system in which the amplification system from input to output is essentially linear.

A further object of the present invention provides output signals as set out above over a dynamic range of inputs in a ratio of one thousand to one.

Yet another object of the present invention to provide a output representing muscle activity, the output changing linearly with the strength of muscle activity.

Still another object of the present invention is to provide the output as set out above for a patient in a system in which an averaging filter is employed to eliminate time integration.

A further object of the present invention is to provide a patient or a therapist with a linear output signal which represents the instantaneous value of muscle activity by an electromyographic biofeedback system which includes an input transducer having a high input impedance, a differential amplifying system to eliminate common mode noise, a band pass filter system for elimination of signals outside the band of electromyographic activity, a rectifying system for selecting the desired information, an averaging filter for providing a signal representative of the instantaneous value of muscle activity and a current controlled oscillator for generating a sequence of pulses, the frequency of which is directly related to the instantaneous value of muscle activity.

It is a feature of the present invention that the output representing muscle activity may be present either in audio or visual form at the option of the patient or therapist, or may be presented in both forms so that the patient may have an audio output while the therapist has a visual representation of muscle activity.

These and other objects, features, and advantages of the present invention will become more apparent by reference to the following description and drawing.

BRIEF DESCRIPTION OF THE DRAWINGS

FIG. 1 is representation of a linear electromyogrphic biofeedback system according to the present invention as is used by a patient.

FIG. 2 is a block diagram of a linear electromyographic biofeedback system according to the present invention.

A linear electromyographic biofeedback system according to the present invention provides the characteristics necessary to feedback learning. These characteristics are instantaneous feedback so that the patient will immediately know the result of his effort as well as the magnitude of the muscle activity resulting therefrom. Second the feedback must be proportional, that is a certain change in muscle activity at one extreme must provide a change in output signal approximately the same as the same change in muscle activity at the other extreme. Third, a wide dynamic range of feedback is necessary to allow the patient to recognize the results of the patient's efforts in a biofeedback learning situation on a single scale. That is frequency increases monotonically with muscle activity and the entire range of muscle activity is contained in a single scale so that the patient does not have to switch from one range to another or any other confusing change which might hinder the feedback learning process.

Referring now to FIG. 1, a patient 8 uses the linear electromyographic biofeedback system 10, according to the present invention as follows: Input transducer 12, is attached to the patient near the area of the muscle which is to be measured for activity. Input transducer 12, has a very high impedance generally in excess of $10^{10}$ megohms.

Figure 3A:
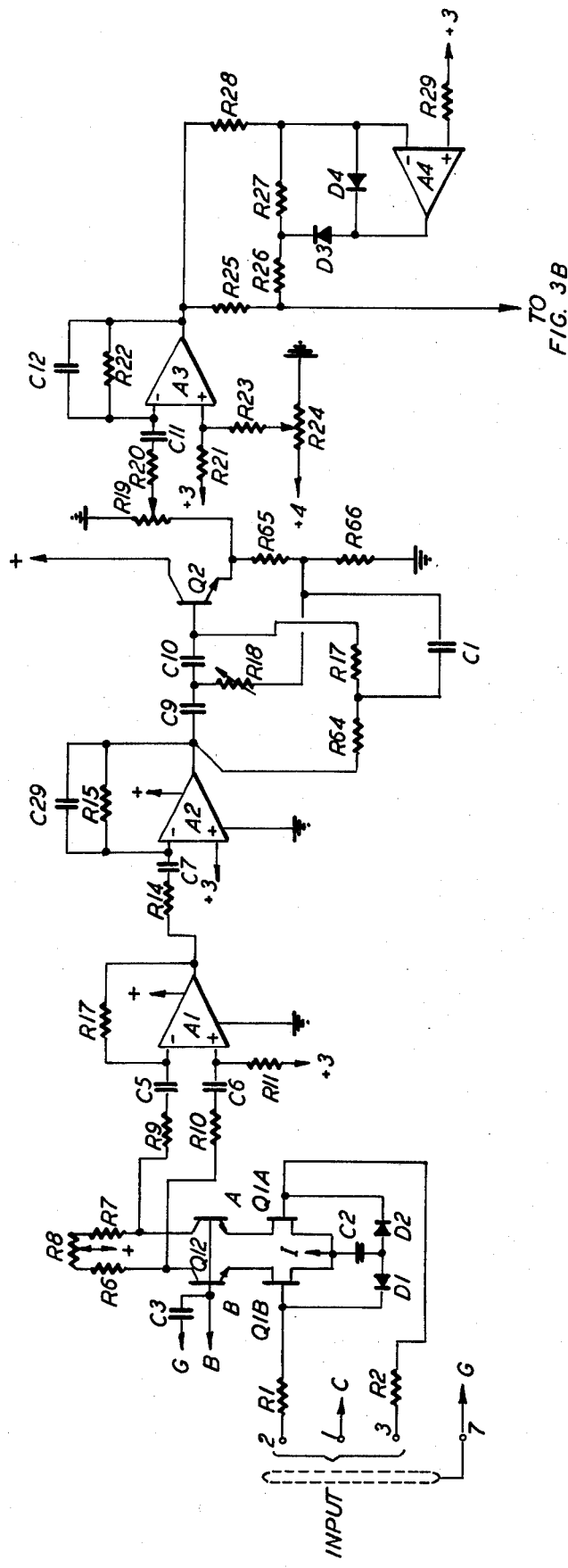
FIG. 3A and 3B are a detailed schematic drawing of a linear electromyographic biofeedback system according to the present invention.

Referring to FIG. 3A, it can seem that input transducer 12, is a balanced transducer. Input transducer 12 is connected to the linear electromyographic biofeedback system 10, by lines 14. The output is presented to the patient through headset 16, being connected to system 10 by line 18. In operation, as the patient attempts to move the muscle whose activity is being measured, the pulse rate which the patient hears in headset 16, will change linearly with the strength of the muscle activity. Thus, a very weak muscle movement might produce a very slow pulse rate in the order of one Hertz and a very strong muscle movement might produce a frequency output in access of 5000 Hertz.

Although not shown in FIG. 1, a display console for use by a therapist may also be connected to the electromyographic biofeedback system 10 so that a therapist may monitor in a digital manner the magnitude of muscle activity.

Referring now to FIG. 2, the individual blocks which are connected together to form the system according to the present invention will be described.

The balanced input from transducer 12, is presented at terminals 21 to protection circuit 22. Protection circuit 22 protects against voltage spikes which could damage the differential amplifier 23. Differential amplifier 23 produces an output signal which is proportional to the difference between the voltage on the input lines 21. The output signal from differential amplifier 23 contains desired signals representing muscle activity as well as noise and other information which is not of interest in the biofeedback system. Therefore, a band pass filter, 24, is connected to the output of differential amplifier, 23, to limit the frequency range which will be passed to the remainder of the system. A common frequency range for electromyographic activity is in the range of 50 to 500 Hertz. Block 24 also has amplification built in to maintain adequate signal levels within the system. The output of the band pass filter is connected to a notch filter 25, which eliminates signals at 60 Hertz which is the power line frequency and a common frequency for undesired signals. The output of notch filter 25, is connected to gain adjustment potiometer, 26, which adjusts the gain level input to a second band pass filter, 27. Band pass filter, 27, operates in a manner similar to band pass filter, 24, but has connected thereto a DC balance adjustment potentiometer, 28, to allow for balancing the system due to individual component variations. The output of band pass filter, 27, is connected to a full wave rectifier, 29, which provides a unidirectional sequence of signals as input to third order averaging filter, 30. Averaging filter 30, has an overshoot adjustment potentiometer, 31, which is used to balance the filter for component variations and to eliminate excessive overshoot on pulse, rise, and fall.

An example of a third order averaging filter which would be used with the present invention is shown in a paper published as a Technical Note in Medical and Biological Engineering, volume 10, pages 559 and 560, Peter Perwgrinus Ltd. 1972. As noted in the introduction of the Technical Note, the third order averaging filter provides a very rapid dynamic response which is very desirable for instantaneous biofeedback.

A filter 30 to be used with the present invention must have the following characteristics. First, the noise throughput must be small relative to the signal from a single muscle unit. Second, the response time must be less then 250 milliseconds. Third, the overshoot response must be less then ten percent. And fourth, the filter must have a monotonic step function response.

The output signal from averaging filter, 30 is connected to a base line control, 32, which is adjusted by the patient to provide a very low or zero output pulse rate with no muscle activity.

The base line control, 32, controls current source, 33, which with current mirror, 34, and current controlled oscilator, 35, convert the output of averaging filter 30, into a digital output in the form of a series of pulses, the repitition rate of which is proportional to the strength of the input muscle activity. The output of current controlled oscilator, 35, is connected to output buffer, 36, which drives earphone, 16.

Of course, if desired, both audio and visual outputs can be obtained from the system.

Figure 3B:
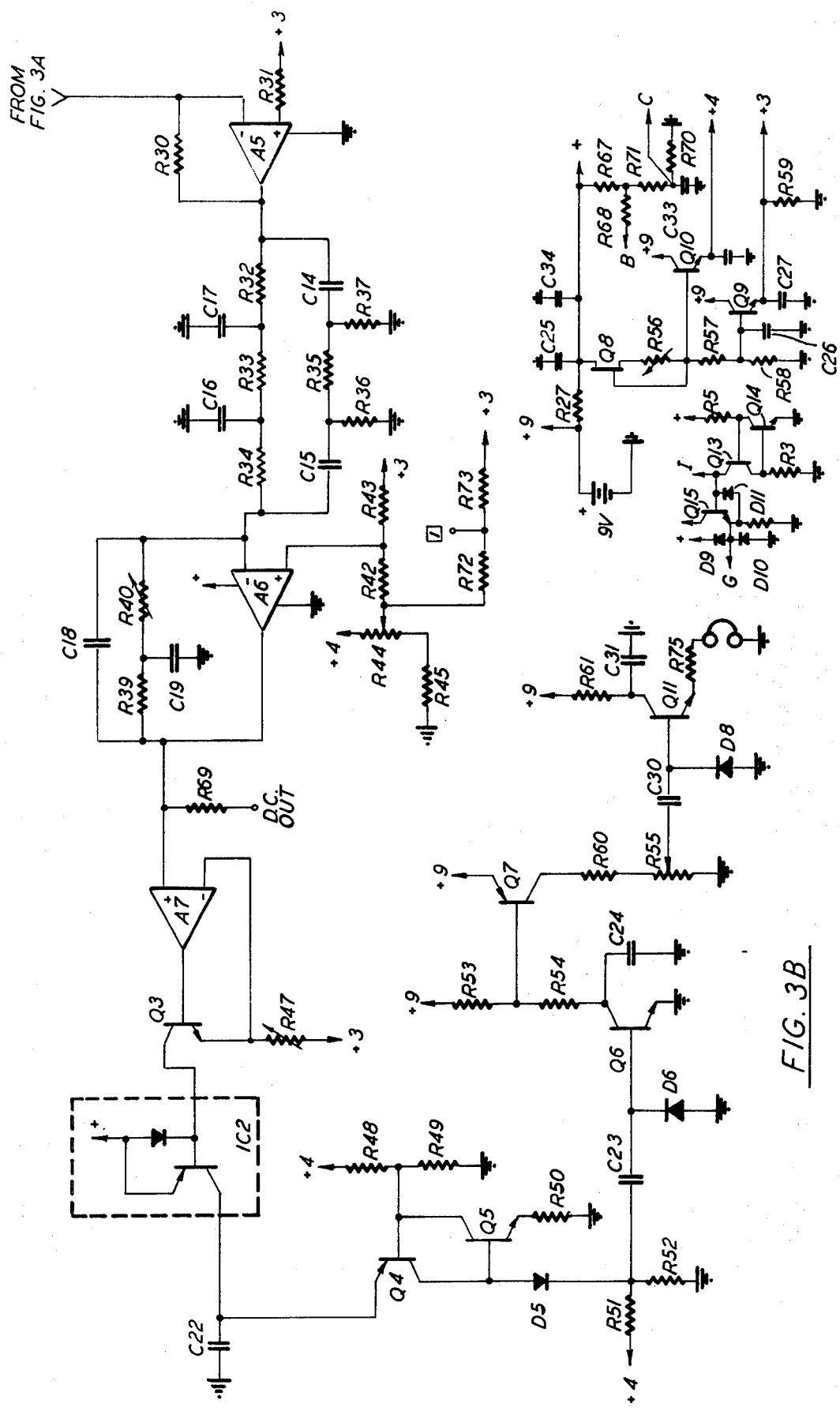

Referring now to FIGS. 3A and 3B, the schematic diagram will be described in relation to the block diagram of FIG. 2.

A balanced high impedance input transducer, 12, is connected at terminals 1, 2, 3, and 7 to protection circuit, 22, which consists of resistors, R1, R2, diodes D1, D2, capacitor C2 and components diodes D9, D10, D11, Q13, Q14, Q15 resistors R3, R4, R5, R66, R68, R70, R71 and capacitor C33. These latter components which form portion of the power supply, provide a current source to supply current to the sources of field effect transistors Q1A and Q1B as well as providing bias voltage for cascade transistors Q12 A and Q12B to maximize common mode rejection.

It is important to maintain the input impedance at as high a level as possible to provide greatest possible common mode rejection for a very small muscle movement.

The respective collectors of Q12A and Q12B are connected through R9,C5 and R10,C6 to the respective minus and plus inputs to differential amplifier A1.

The output of differential amplifier A1 is connected to first band pass filter, 24, which consists of operational amplifier A2 and filter components R14, C7, R15, C29.

The band pass filter, 24, is connected through notch filter C9, C10, R17, R18, R64 and C1 through emitter follower to Q2, which has an output taken from gain adjustment potentiometer, R19, to the second band pass filter, 27, which includes DC balance adjustment potentiometer, R24. The band pass characteristics of second band bass filter, 27, are controlled by resistors, R20 and R22 and capacitors, C11 and C12.

Full wave rectifier 29 shown in FIG. 2 includes resistors R25, R26, R27, R28, R29, R30, R31, diodes D3 and D4 and operational amplifiers A4 and A5. As with any full wave rectifier, the output of operational amplifier A5 is a unidirectional signal which contains the electromyographic information representing muscle activity. The output of the full wave rectifier 29 is connected to averaging filter 30.

Averaging filter 30 consists of filter components R32, R33, R34, R35, R36, R37 capacitors C14, C15, C16, C17 operational amplifier A6, filter C18, C19, R39, R40 and base line control R42, R43, R44 and R45. Variable resistor R44 is the base line adjustment potentiometer. A voltage divider consisting of resistors R72 and R73 provides a reference point 1 at the junction of R72 and R73 which is the return connection for a visual display device which may be connected to the DC output from averaging filter 30.

A visual display device such as an analog volt meter or a group of digital indicators each of which indicates a successively higher level of muscle activity maybe connected between the DC out connection and the junction of resistors R72 and R73.

The output of averaging filter 30 is connected to operationl amplifier A7 which with transistor Q3 and resistor R47 operate as constant current source 33. Variable resistor R47 provides a gain adjustment for current source 33. The collector of current source transistor Q3 is connected to IC2 which operates as current mirror 34.

The output of current mirror, 34, is connected to relaxation oscillator Q4, Q5, C22, R48, R49, R50, R52, and D5 which provides a pulsed output controlled by the voltage present at the positive input to current source, 33.

The output of the relaxation oscillator is connected through C23 to amplifier Q6 which with Q7 and Q11 provide a buffer amplifier for amplifying the audio signal for presentation to headphones, 16.

While the invention has been described with respect to a preferred embodiment thereof, there are many variations in specific circuit implementation which may be used to provide the funtional element required for applicants invention.

It will be understood by those skilled in the art that many variations in specific implementation may be made without departing from the spirit or scope of the invention.

What is claimed is:

1. An electromyographic biofeedback system for indicating magnitude of muscle activity by measuring voltage on a skin surface adjacent a muscle which is to be measured; comprising:
   a transducer adapted to be positioned on a skin surface adjacent a muscle which is to be measured;
   high input impedance differential linear amplifier means connected to said transducer for amplifying voltages representing magnitude of muscle activity; said amplifier means eliminating common mode noise and maximizing said voltage representing muscle activity, said amplified means providing a linear amplification of muscle activity voltage over a dynamic range of at least one thousand times a smallest measurable input voltage;
   filter means connected to the output of said amplifier means comprising one or more band pass filters adapted to pass a band of frequencies in which the greatest amount of electromyographic activity occurs, for filtering out unwanted information and passing signals in a predetermined desired range of frequencies, said filter means further comprising a rejection filter adapted to reject signals and noise occurring in commonly used electrical power line frequencies;
   detection means connected to the output of said filter means for detecting voltages representing muscle activity;
   averaging filter means connected to an output of said detection means, said averaging filter means having a rise time of less than 250 milliseconds and having an overshoot of less than 10 percent of maximum signal value, said averaging filter means adapted to provide an output signal representing an instantaneous value of voltage corresponding to muscle activity;
   oscillator means connected to the output of said averaging filter means for converting voltage representations of magnitude of muscle activity to a sequence of signals in the audio frequency range; and
   output transducer means for converting said sequence of signals in the audio frequency range into an audible signal for recognition by human being.

2. A system according to claim 1, wherein said oscillator means further comprises a current controlled oscillator responsive to an output of said averaging filter means.

3. A system according to claim 1, further comprising:
   voltage protection means connected to said transducer, the output of said voltage protection means being connected to said amplifier means for amplifying signals representing highest electromyographic activity;
   said detection means comprising rectifier means connected to the output of said filter means for providing a unidirectional signal representing muscle activity;
   said averaging filter means connected to the output of said rectifier means for providing a signal for controlling a current controlled oscillator in accordance with an instantaneous value of input voltage representing muscle activity; and,
   said oscillator means comprising a current controlled oscillator connected to the output of said averaging filter means for producing an output signal which may be used by a patient for biofeedback of muscle activity.

* * * * *